United States Patent [19]

Lastick et al.

[11] Patent Number: 5,372,939
[45] Date of Patent: Dec. 13, 1994

[54] **COMBINED ENZYME MEDIATED FERMENTATION OF CELLULOUS AND XYLOSE TO ETHANOL BY *SCHIZOSACCHAROYCES POMBE*, CELLULASE, β-GLUCOSIDASE, AND XYLOSE ISOMERASE**

[75] Inventors: Stanley M. Lastick, Longmont; Ali Mohagheghi, Northglen; Melvin P. Tucker, Lakewood, all of Colo.; Karel Grohmann, Winter Haven, Fla.

[73] Assignee: The United States of America as represented by the United States Department of Energy, Washington, D.C.

[21] Appl. No.: 28,592

[22] Filed: Mar. 8, 1993

Related U.S. Application Data

[63] Continuation of Ser. No. 672,984, Mar. 21, 1991, abandoned.

[51] Int. Cl.$^5$ ............................................. C12P 7/12
[52] U.S. Cl. ............................. 435/165; 435/161; 435/162; 435/163; 435/171; 435/255.1
[58] Field of Search ..................... 426/11, 18, 20, 21; 435/161, 163, 165, 162

[56] References Cited

U.S. PATENT DOCUMENTS

| | | | |
|---|---|---|---|
| 3,990,944 | 11/1976 | Gauss et al. | 435/165 |
| 4,009,075 | 2/1977 | Hoge | 435/165 |
| 4,326,032 | 4/1982 | Grove | 435/163 |
| 4,326,036 | 4/1982 | Hayes | 435/163 |
| 4,368,268 | 1/1983 | Gong | 435/161 |
| 4,472,501 | 9/1984 | Takasawa et al. | 435/163 |
| 4,490,468 | 12/1984 | Gong et al. | 435/161 |
| 4,511,656 | 4/1985 | Gong | 435/161 |
| 4,628,029 | 12/1986 | Eveleigh et al. | 435/165 |
| 4,663,284 | 5/1987 | Jeffries | 435/161 |
| 4,840,903 | 6/1989 | Wu | 435/165 |

OTHER PUBLICATIONS

Motoo, A. et al., "Conversion of rice straw to ethanol by simultaneous saccharification and fermentation", Chemical Abstracts 103 (23), 19492 6v, 1985.

*Primary Examiner*—Marian Knode
*Attorney, Agent, or Firm*—Kenneth Richardson; Thomas G. Anderson; William R. Moser

[57] ABSTRACT

A process for producing ethanol from mixed sugar streams from pretreated biomass comprising xylose and cellulose using enzymes to convert these substrates to fermentable sugars; selecting and isolating a yeast *Schizosaccharomyces pombe* ATCC No. 2476, having the ability to ferment these sugars as they are being formed to produce ethanol; loading the substrates with the fermentation mix composed of yeast, enzymes and substrates; fermenting the loaded substrates and enzymes under anaerobic conditions at a pH range of between about 5.0 to about 6.0 and at a temperature range of between about 35° C. to about 40° C. until the fermentation is completed, the xylose being isomerized to xylulose, the cellulose being converted to glucose, and these sugars being concurrently converted to ethanol by yeast through means of the anaerobic fermentation; and recovering the ethanol.

4 Claims, 1 Drawing Sheet

FERMENTATION OF 5% XYLOSE + 10% CELLULOSE

CONTROL FERMENTATIONS: 5% XYLOSE, 10% CELLULOSE

COMBINED ENZYME MEDIATED FERMENTATION OF CELLULOUS AND XYLOSE TO ETHANOL BY *SCHIZOSACCHAROYCES POMBE*, CELLULASE, β-GLUCOSIDASE, AND XYLOSE ISOMERASE

CONTRACTURAL ORIGIN OF THE INVENTION

The U.S. Government has rights in this invention under Contract No. DE-ACO2-83CH10093 between the U.S. Department of Energy and the Solar Energy Research Institute, a Division of Midwest Research Institute.

This is a continuation of application Ser. No. 672,984 filed Mar. 21, 1991 abandoned.

BACKGROUND OF THE INVENTION

1. Field of the Invention

The invention relates to a process that combines a simultaneous saccharification and fermentation (SSF) process and a simultaneous fermentation and isomerization of xylose (SFIX) process to provide a simpler and reduced cost process for producing ethanol. In particular, the invention pertains to an improved process for producing ethanol from a mixed stream of xylose and cellulose and includes fermenting the mixed stream using a cellulase and xylose isomerase enzyme, under predetermined conditions, and includes simultaneously saccharifying the cellulose while fermenting the soluble sugars produced, and concurrently isomerizing the xylose while fermenting the xylulose as it is produced.

2. Description of the Prior Art

U.S. Pat. No. 4,663,284 to Jeffries discloses a process for producing ethanol from D-xylose by fermentation with xylose metabolizing yeasts, wherein small quantities of glucose are added to the fermentation medium during the fermentation process; however, the process is not an enzyme mediated process. Yeast strains can ferment xylose if oxygen is allowed to be present in the fermentation. The process of Jeffries further disclose that the addition of glucose to these oxygen mediated fermentations improves the yield of the fermentation; however, cellulose fermentation is not taught or included.

U.S. Pat. No. 4,511,656 to Gong pertains to a method for producing ethanol directly from D-xylose through fermentation of D-xylose by yeast mutants. The process further provides for directly and simultaneously obtaining ethanol from a mixture of cellulose and hemicellulose through yeast fermentation of D-glucose and D-xylose; however, these are oxygen mediated fermentations of xylose and are supplemented by the addition of glucose, as the sugar or as a hydrolysate containing glucose. In addition to oxygen being required, no enzymes are used and cellulose is not fermented.

In U.S. Pat. No. 4,490,468 to Gong et al., there is described an anaerobic fermentation of xylulose previously obtained by isomerization of xylose, and example 6 thereof briefly mentions the possibility of simultaneous isomerization and fermentation of xylose; however, the process is not combined in any way with the fermentation of cellulose.

U.S. Pat. No. 4,368,268 to Gong relates to a process for the production of ethanol from xylulose. The process includes isomerizing the xylose to xylulose and fermenting the xylulose to ethanol. Essentially, this process is the fermentation of xylose or xylose and other sugars in hemicellulose hydrolysates by mutant strains of yeast, either aerobically or anaerobically; however, hemicellulose does not refer to cellulose but to extracts obtained by pretreatment of materials that contain cellulose. The sugars obtained are soluble sugars (in most cases mostly xylose). Cellulose is not soluble and must be enzymatically digested to produce soluble sugars. Further, fermentations of xylose or hemicellulose, whether or not the hemicellulose contains some glucose, is not cellulose fermentation, and the fermentations in this patent are not anaerobic but oxygen mediated rather than enzyme mediated fermentations.

U.S. Pat. No. 4,840,903 to Wu discloses a process for the production of ethanol by a fungal strain capable of slowly degrading and fermenting cellulose, xylose, and a number of other sugars. Like simultaneous saccharification and fermentation (SSF) of cellulose, cellulase enzymes were added to the fermentations to produce glucose from cellulose; however, the fermentations are not a combination of enzymatic isomerization of xylose to xylulose a fungal strain rather than ethanol tolerant yeast was used for the fermentation, and fungal strains take much longer to grow and ferment, and these longer lengths of time or slow rates are unacceptable for industrial purposes.

In biomass materials, cellulose and hemicellulose are the two most abundant and renewable raw organic compounds, and together they compose above 70 percent of the entire world's plant biomass on a dry weight basis. These raw materials are widely available in waste from agricultural, forest, vegetable and food process sources, and the efficient recycling of these wastes to useful products, such as ethanol, would help to reduce disposal problems as well as provide an abundant and cheap source of fuel.

SUMMARY OF THE INVENTION

It is an object of the invention to produce ethanol from xylose using cellulosic biomass waste without having to ferment separately a stream containing soluble xylose in an enzyme mediated process.

A further object of the invention is to produce ethanol from xylose using cellulosic biomass waste without having to separately ferment the cellulose in the feedstock.

A yet further object of the invention is to produce ethanol using cellulosic biomass waste by combining a simultaneous fermentation and isomerization of xylose (SFIX) process and a simultaneous saccharification and fermentation (SSF) process to simplify the entire biomass to ethanol process and to significantly reduce costs because of significantly reduced equipment requirements.

In general, the objectives of the invention are accomplished by producing ethanol from a mixed stream of xylose and cellulose using enzymes to convert these carbohydrates to fermentable sugars under predetermined conditions. This is done by the simultaneous conversion of cellulose to glucose, using cellulase enzymes, and the conversion of xylose to xylulose, using the enzyme xylose isomerase in the presence of *Schizosaccharomyces pombe* ATCC No. 2476. The enzymatic processes allow for these fermentable sugars, glucose and xylulose, to be converted by yeast to ethanol in the same fermentation. The continuous conversion of the sugars to ethanol by the fermenting yeast is key to the process because the activities of the enzymes are inhibited in the presence of their products, glucose (and the disaccharide cellobiose) and xylulose.

DETAILED DESCRIPTION OF THE INVENTION

It is a discovery of the invention that the process of converting biomass to ethanol can be simplified via a process of combining a simultaneous saccharification and fermentation process (SSF) and a simultaneous fermentation and isomerization of xylose process (SFIX). By combining the two processes for separate cellulose and xylose fermentation, there is a significant reduction in costs and equipment. Combining the two processes allows for fermentation of mixed sugar streams of pretreated biomass without the need for separation of the xylose and cellulose components. Further, since much higher ethanol concentrations are obtained with the combined process of the invention, as compared with separate fermentations, the cost of ethanol recovery is significantly reduced.

The fermentations of the process of the invention are conducted under totally anaerobic conditions and sampling is performed under nitrogen in order to maintain strict anaerobiosis. The fermenters are continuously controlled to maintain a pH range between about 5.5 and about 6.0, preferably at a pH of 5.75 by the automatic addition of 1M of NaOH. Preferably, the pH is kept at 5.75 during the fermentations, the temperature range is automatically maintained between about 35° C. to about 40° C. preferably at a temperature of 37° C.

The ethanol produced was measured by gas chromatography (GC) and the soluble sugars were measured by high performance liquid chromatography (HPLC).

The invention can best be understood by referring to the examples.

SFIX/SSF FERMENTATION OF XYLOSE/CELLULOSE MIXTURE

Example I

Figure 1:
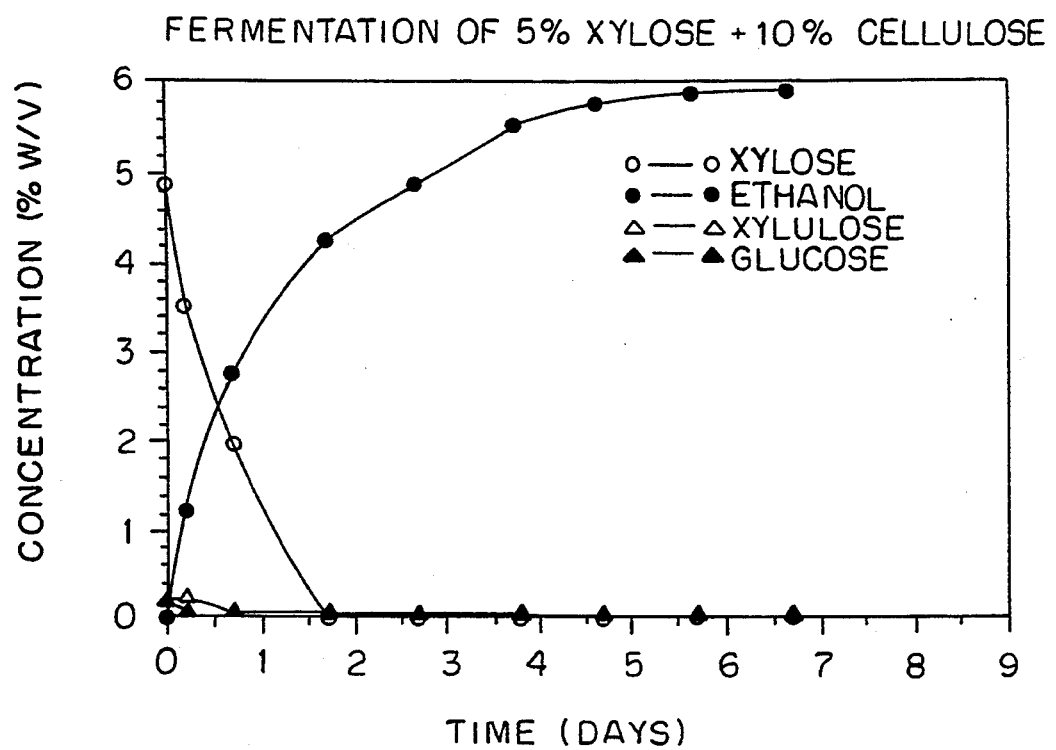
FIG. 1 depicts the yield of ethanol from fermentation of 10% (w/v) cellulose and 5% (w/v) xylose performed at 37° C. at pH values of 5.5 to 6 using *Schizosaccharomyces pombe* ATCC 2476 (NRRL Y-164) and commercial cellulase (Genencor 2000 IFPU/L), β-glucosidase (2000 IU/L) and xylose isomerase (25 1U/L) enzymes.

Substrates of 10% (w/v) cellulose Solkafloc and 5% (w/v) xylose were fermented using *Schizosaccharomyces pombe* (a sample of this strain under the Budapest Treaty, is deposited with the culture collection of American Type Culture Collection, and is available to the public under ATCC No. 2476 at 12301 Parklawn Drive, Rockville, Md. 20852) (NRRL Y-164) under anaerobic conditions at 37° C., while the pH was kept between 5.5 and 6.0 by automatic addition of small amounts of 1M NaOH, using the plural ferment of the enzymes cellulase (Genecor, 2000 IFPU/L) β-glucosidase (2000 IU/L) and xylose isomerase (Novo, 25 IU/L). Both substrates were totally fermented and a final yield of 59 g/L of ethanol was produced. The stoichiometric maximum yield of ethanol was calculated to be 56.8 g/L from 10% (w/v) cellulose and 25.6 g/L from 5% (w/v) xylose, or a total of 82.6 g/L. Therefore, the final yield of 59 g/L is 72% of the theoretical maximum (FIG. 1).

Analysis of sugar concentrations, using high performance liquid chromatography, showed that the xylose was completely consumed within 2 days, and this rate of consumption is as fast as when xylose is fermented alone using the simultaneous fermentation and isomerization of xylose (SFIX) process. This result, and other results that used the SFIX to ferment xylose/glucose mixtures show that the presence of glucose does not inhibit the fermentation of xylose.

Example 2

Figure 2:
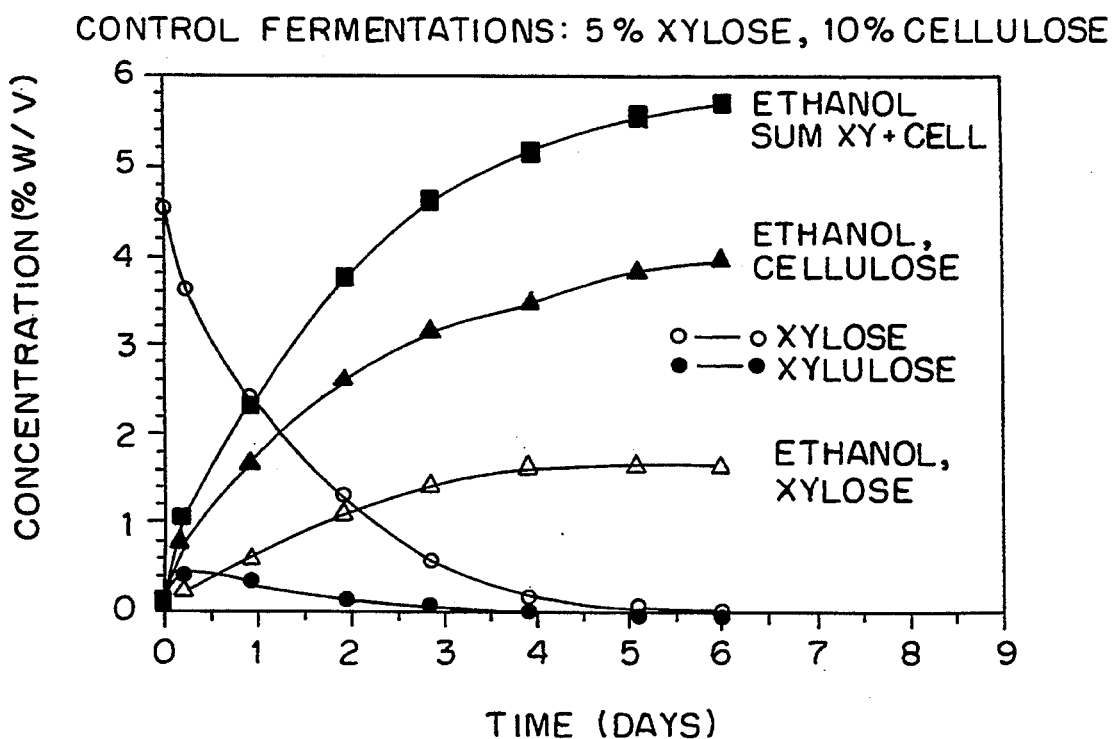
FIG. 2 depicts control fermentation of xylose and cellulose performed separately under the conditions used in the combined fermentation.

Control fermentations of 10% (w/v) cellulose Solkafloc and 5% (w/v) xylose were performed under the same conditions as those used in the combined fermentations of example 1. As can be seen from FIG. 2, the total amount of ethanol produced by the separate fermentations was approximately the same amount as in the combined fermentation, indicating that no decrease in ethanol occurred when the processes were combined.

As a result of the invention process,
which allows processing of mixed sugar streams from biomass containing both xylose and cellulose without expensive separate fermentations, large amounts of ethanol can be economically provided for fuel from an almost unlimited supply of substrates.

The foregoing examples are illustrative only of the principles of the invention, and numerous modifications, equivalents, and changes will readily occur to those skilled in the art without departing from the spirit and scope of the invention, which is defined by the claims that follow.

The embodiments of the invention in which an exclusive property is claimed are as follows:

1. A process for producing ethanol from mixed streams from biomass comprising:
   selecting as substrates either xylose and cellulose or xylan and cellulose;
   selecting a plural ferment comprising a mixture of *Schizosaccharomyces pombe* ATCC No. 2476, cellulase, betaglucosidase and xylose isomerase wherein said plural ferment can isomerize xylose and ferment xylulose as it is being formed to ethanol and simultaneously saccharily cellulose to glucose and ferment glucose to ethanol;
   loading said substrates with said plural ferment;
   fermenting said loaded substrate under anaerobic conditions at a pH range of between about 5.5 to about 6.0 and at a temperature range of between about 30° C. to about 45° C., until any xylose in the mixture is isomerized to xylulose as it is produced, and any xylulose is fermented as it is produced to ethanol, while in the same fermentation, glucose is fermented to ethanol; and
   recovering the ethanol.

2. The process of claim 1, wherein said substrates are cellulose and xylose.

3. The process of claim 2, wherein said temperature is between 35° C. and 40° C.

4. The process of claim 3, wherein said enzymes are in amounts of about 2,000 IFPU/L cellulase, 2,000 IU/L betaglucosidase and 25 IU/L xylose isomerase.

* * * * *